United States Patent [19]

Dominguez et al.

[11] Patent Number: 4,971,077
[45] Date of Patent: Nov. 20, 1990

[54] ON-LINE TOBACCO EVALUATION SYSTEM AND METHOD

[75] Inventors: Luis M. Dominguez; Calvin W. Henderson, both of Winston-Salem, N.C.

[73] Assignee: R. J. Reynolds Tobacco Company, Winston-Salem, N.C.

[21] Appl. No.: 388,457

[22] Filed: Aug. 2, 1989

[51] Int. Cl.⁵ .................... A24C 5/00; G01F 1/00; G01J 3/42
[52] U.S. Cl. .................... 131/108; 131/109.1; 131/905; 131/909; 250/356.1; 250/359.1; 250/341; 356/319
[58] Field of Search ............ 131/108, 109.1, 905, 131/909; 250/356.1, 359.1, 341; 356/319

[56] References Cited

U.S. PATENT DOCUMENTS

| | | |
|---|---|---|
| 2,752,815 | 7/1956 | Batchelor . |
| 3,831,610 | 8/1974 | Wochnowski et al. . |
| 3,875,383 | 4/1975 | Somerville et al. . |
| 3,962,581 | 7/1976 | Zimmerman . |
| 4,037,970 | 7/1977 | Webster et al. . |
| 4,082,950 | 4/1978 | Chen . |
| 4,220,164 | 9/1980 | Lorenzen ..................... 131/909 |
| 4,228,393 | 10/1980 | Pile . |
| 4,236,640 | 12/1980 | Knight . |
| 4,363,968 | 12/1982 | McGowan et al. . |
| 4,449,819 | 5/1984 | Krause . |
| 4,540,282 | 9/1985 | Landa et al. . |
| 4,582,992 | 4/1986 | Atwell et al. . |
| 4,609,108 | 9/1986 | Hristozov et al. . |
| 4,633,087 | 12/1986 | Rosenthal et al. . |
| 4,640,614 | 2/1987 | Roberts et al. . |

OTHER PUBLICATIONS

Isaac Landa, "Visible (VIS) Near Infra Red (NIR) Rapid Spectrometer for Laboratory and On Line Analysis of Chemical and Physical Properties"; SPIE vol. 665, Optical Techiques for Industrial Inspection, pp. 286–289 (1969).
"Food Processors Bet On On-Line NIR Analysis for Big Gains"; Food Engineering (Mar. 1988).
K. J. Rashmawi et al; "Near Infrared Analyzer Reveals Moisture in Minutes"; Chemical Processing, (Jun. 1988).

Primary Examiner—V. Millin
Attorney, Agent, or Firm—Grover M. Myers

[57] ABSTRACT

The present invention comprises a product moving apparatus for moving a tobacco product, a vertical feeder tube for metering the tobacco product onto the product moving apparatus at a predetermined rate, a system for maintaining a predetermined height of the tobacco product in the feeder tube, and an infrared detection apparatus connected to the feeder tube to detect the concentration of menthol in the tobacco product.

22 Claims, 5 Drawing Sheets

ON-LINE TOBACCO EVALUATION SYSTEM AND METHOD

BACKGROUND OF THE INVENTION

1. Field of the Invention

This invention relates to a method and apparatus for testing in-process materials and in particular relates to real-time testing for the concentration of a number of components, such as menthol, water, nicotine, sugars, and the like in a tobacco product.

2. Discussion of Related Art

In the production of tobacco products such as menthol cigarettes, the concentration of components such as moisture, nicotine, sugars, menthol, and the like is very important and must be monitored. Chemical processing and quality control has usually been accomplished by collecting samples from the factory floor and taking them to a laboratory at a remote site for analysis. The results usually arrive too late for any significant quality control to be effected. The more typical situation, in fact, is that the product is in the distribution pipeline before results arrive form the laboratory. This reduces any effort at quality assurance to an audit and lengthens the time necessary to perform process control studies.

Near infrared reflectance (NIR) spectroscopy has been used extensively in the agricultural industry for the past twenty years for the measurement of compounds such as sugars, and water. Filter and full spectrum analyses have been used extensively in the cigarette industry for off-line applications. Also, the cigarette industry has used this technique for on-line inspection of tobacco for the presence of moisture, although this is not a "full spectrum" analysis. Full spectrum analyses have not been used for active real-time applications in tobacco processing.

SUMMARY OF THE INVENTION

Recent advances in instrumentation have permitted the use of traditional laboratory equipment in the factory. The advent of integrated circuits, miniaturized computer hardware, and sturdier optics has allowed for smaller and more rugged equipment to be used in the plant. This has the potential of allowing for real process control with rapid generation of relevant measurement and fast manipulation of process variables.

One object of the present invention is to provide a system which can determine the concentration of a component in a tobacco product as the tobacco product moves through a process line.

Another object of the present invention is to provide a tobacco product evaluation system which can be incorporated into an existing process with a minimum of alteration or disruption of the line.

A further object of the present invention is to provide a tobacco product evaluation system which can be used to control a process of the process line.

Another object of the present invention is to provide a tobacco product evaluation system which provides a substantial improvement of tobacco product made with its use.

In accordance with the above and further objects, the present invention comprises a product moving apparatus for moving a tobacco product, a vertical feeder tube for metering the tobacco product onto the tobacco product moving apparatus at a predetermined rate, a system for maintaining a predetermined height of the tobacco product in the feeder tube, and an near infrared measurement apparatus connected to the feeder tube to detect the concentration of a component in the tobacco product.

The infrared detection apparatus may comprise a near infrared reflectance spectrometer having a monochromator to distinguish absorption by the component to be such as menthol, from absorption by a carrier for the component, such as a menthol carrier, or water, or other endogenous absorption of tobacco.

The invention may also include a cigarette making machine, the tobacco product being cigarette tobacco and the moving apparatus being constructed and arranged to feed the cigarette tobacco to the making machine.

The invention may also include a component application apparatus to add a component such as water, menthol, and sugars to tobacco to produce the tobacco product and a controller for controlling the operation of the component application apparatus in response to the infrared detection apparatus to maintain the concentration of the component in a predetermined range.

In other forms, the invention comprises a vertical metering tube for metering a tobacco product, apparatus for maintaining a predetermined height of tobacco product in the vertical metering tube, apparatus for receiving tobacco product from the vertical metering tube at a predetermined rate, apparatus for sensing a flow of tobacco product through the vertical metering tube, apparatus for determining the concentration of a predetermined component of the tobacco product while the product is flowing through the metering tube, and apparatus for interrupting the operation of the determining apparatus if the flow of tobacco product through the metering tube stops.

The present invention also includes a method of determining the concentration of a predetermined component in tobacco while the tobacco is moving through a processing line.

BRIEF DESCRIPTION OF THE DRAWINGS

The above and other objects of the present invention will become more readily apparent when the invention becomes more fully understood from the detailed description to follow, reference being had to the accompanying drawings in which like reference numerals represent like parts throughout and in which.

DETAILED DESCRIPTION OF THE PREFERRED EMBODIMENTS

The in-process tobacco product evaluation and control system 10 of the present invention is shown in FIG.

Figure 1:
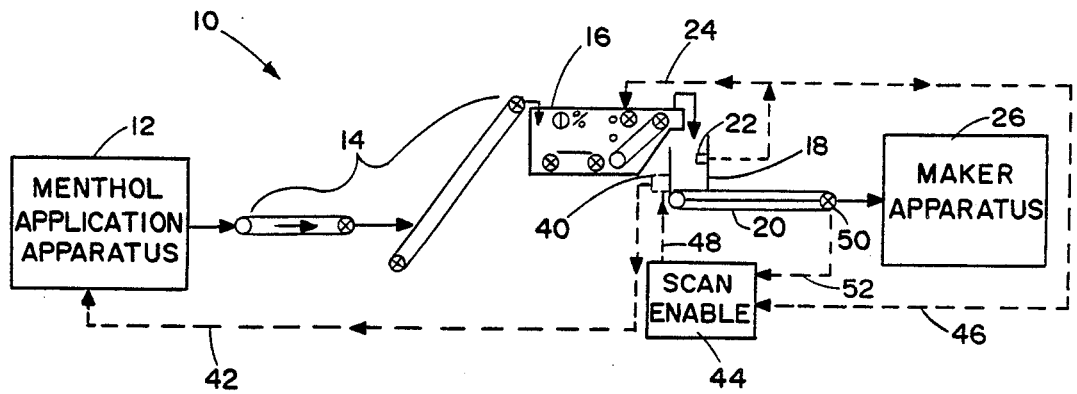
FIG. 1 is a partial block diagram of the present invention showing product flow with solid arrows and control information flow in dotted arrows.

1. This system is shown in use in a cigarette manufacturing line but could be used in many other types of processes. The system includes a component application apparatus 12 which receives tobacco in a conventional manner and adds a component to the tobacco. At various stages of the process, different components are added. These include, water, sugars, menthol and the like. This type of operation is conventional in the tobacco industry and will not be described in detail here. In FIG. 1, a menthol application apparatus is shown. Generally, menthol is the last component to be added to the tobacco before it is passed to the cigarette maker 26. The mentholated tobacco is passed via a conveyor system 14 to a bulker 16 where it is stored for a period of time, i.e. several hours, in order for the amount of menthol to equilibrate uniformly throughout the treated tobacco. It is noted that, as discussed below, the sampling of the tobacco is done after the bulker 16. However, it is also within the scope of the invention to perform the sampling measurement between the menthol application apparatus and the bulker 16. It is also noted that bulkers are well known in the industry so that a detailed description of the operation of bulker 16 will not be given here.

When the tobacco is ready for use, it is delivered from bulker 16 to a metering tube 18. As will be apparent to those skilled in the art, the bulker 16 may directly feed the metering tube, or there may be intervening conveyors. This tobacco is metered from tube 18 onto a conveyor 20. Conveyor 20 may be any conventional conveyor apparatus such as a belt conveyor or a pneumatic conveyor tube. In the case of a pneumatic conveyor tube, a rotating rake (not shown) may be used to move the tobacco from the bottom of the metering tube 18 into the conveyor. The use of metering tubes with belt and pneumatic conveyors is conventional in the industry. In the case of a belt conveyor, as shown, the metering tube 18 is normally located at a height above the conveyor 20 which is the same as the front-to-back depth dimension of the metering tube. As the conveyor belt moves, the metering tube 18 will lay a bed of tobacco on the moving conveyor belt 20 which has a height or thickness the same as the front-to-back depth of the metering tube.

A sensor 22 is attached to the metering tube 18 to determine the height of tobacco in the metering tube. Sensor 22 may be a light sensor, a capacitive sensor or the like, or a series of such sensors. The output from sensor 22 is fed to the control for the bulker 16 through a control line indicated at 24 to control the feed rate of the bulker into the metering tube 18. In this way, the height of tobacco in the metering tube 18 is kept substantially constant.

Figure 2:
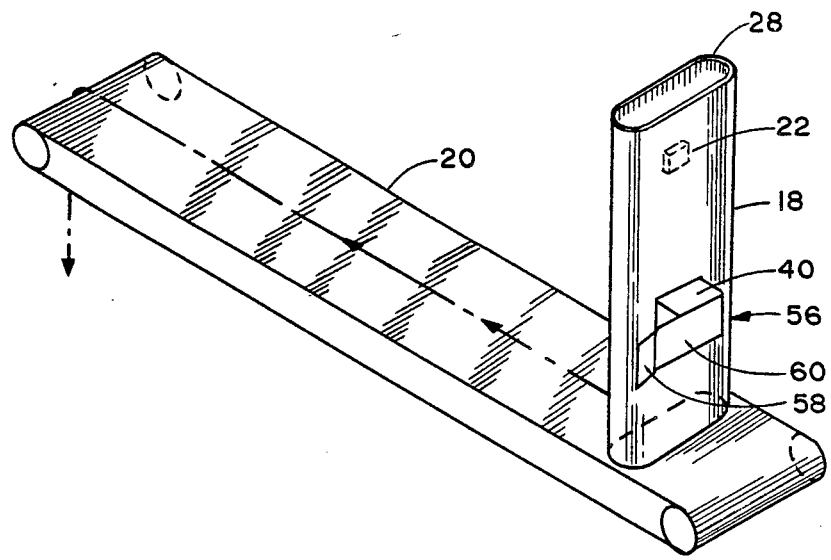
FIG. 2 is a perspective view showing a typical metering tube and cigarette maker feeder as may be used in the present invention.

FIG. 2 shows more clearly the configuration of the metering tube 18, conveyor 20 and feeders for the cigarette maker 26. As shown, the metering tube 18 is a vertical chute which is designed to receive tobacco in an open upper end 28. The tobacco is deposited on the conveyor 20 which transports it to the next processing station.

Returning to FIG. 1, according to the invention, the concentration of components including menthol, moisture, sugars, and nicotine in the tobacco in metering tube 18 is detected by a detector 40 attached to metering tube 18. Detector 40 can be a conventional full spectrum near infrared (NIR) reflectance spectrometer fitted to the side of metering tube 18. Any of various full spectrum NIR apparatuses, as will be well known to those skilled in the art, are preferably employed in the practice of this invention, such as a Pacific Scientific Model 7000 "Dynascan" analyzer, an L. T. Industries Quantum 1200, or the like. This instrument may include a stepper motor driven tilting-filter wheel that revolves at approximately 5 revolutions per second to accomplish a dispersion of white light into component wavelengths; or it may be equipped with an oscillating holographic grating or other continuous light dispersing optical elements. In the tilting filter wheel embodiment, in the five revolutions the instrument obtains sample scans and reference scans as dictated by the control program. In all cases, the light from a quartz-halogen lamp or other lamp with a similar broad spectral output, strikes the filters in the dispersing optical element at an angle. The wavelength of light which passes through the tilting filter or reflects from the oscillating grating is a function of the instantaneous angle between the dispersing element and the light. Bandpasses of plus or minus 15 nm. are typical for filter instruments, and less than 10 nm. are typical for reflectance instruments. Quadrature detection is employed with standard lead sulfide detectors.

Both instruments mentioned above run on control and analysis software purchased from their respective manufacturers. A microcomputer such as an IBM/AT computer, ruggedized for use in the factory, is used to un the software.

Detection device 40 produces an output signal indicative of the concentration of components in the tobacco of metering tube 18. This signal is sent through line 42 to a controller for the apparatus adding the component. In the case of menthol, a signal sent to the menthol application apparatus 12 to control the concentration of menthol so that it is within a desired range.

It will be understood that a full spectrum NIR analysis is carried out to enable a determination of the concentration of several components in the tobacco. In this regard, the concentration of the desired component or components in the tobacco can be determined using a predictive equation derived from the NIR spectra using multivariate linear regression. In the case of some components, such as menthol, the predictive equation would be blend sensitive but, nevertheless, highly accurate.

In order to ensure that the reading taken by detection device 40 is accurate, it is preferable to ensure that the compaction of tobacco in the metering tube 18 is relatively constant. Clearly, a reflectance taken from relatively densely packed tobacco would be different from that taken from relatively loosely packed tobacco as can be shown from the Kubelka-Munk Theory of Diffuse Reflectance. The metering tube 18 provides an excellent position to take concentration readings since the requirement for constant density for an accurate reading is also a requirement for proper operation of the metering tube. This is the purpose of the height sensor 22, discussed above. As long as the height of tobacco in tube 18 is within predetermined limits as indicated by sensor 22, the tobacco density at any given location below the sensor over time will be relatively constant. Consequently, the detection device 40 is placed below the sensor 22.

A scan enable circuit 44 receives the output from the sensor 22 through a line 46 and enables operation of the sensing device 40 through line 48 only when the tobacco height is within the specified limits. This ensures an accurate reading.

Another consideration for taking accurate readings is that the tobacco be moving through the metering tube at a predetermined rate. If, for example, progress of the tobacco through tube 18 is halted, the signal sent through line 42 to control the application of a component will not change even if more or less of the component is added. This problem is resolved by monitoring the conveyor 20 through a tachometer 50 attached to the drive for conveyor 20. A signal from the tachometer 50 is sent through line 52 to scan enable circuit 44 which will disable sensing device 40 if the conveyor stops for any reason. Alternatively, the signal can be derived directly from the current driving the conveyor motor.

Figure 3:
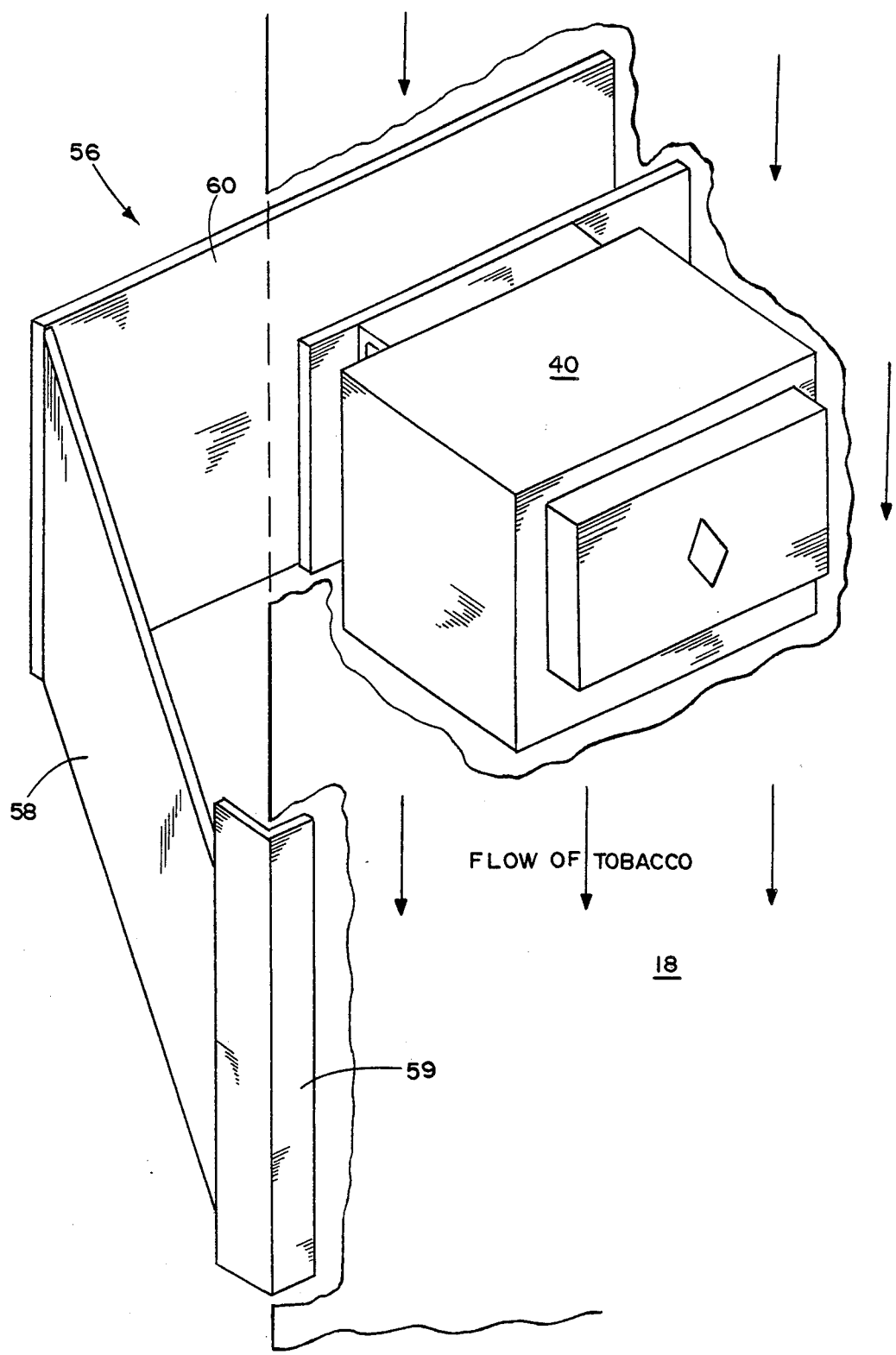
FIG. 3 is a part fragmentary view showing a near infrared detection apparatus and a bracket for attaching the near infrared detection apparatus to a metering tube.

As shown in FIGS. 2 and 3, a bracket 56 is attached to the outside of the metering tube 18 to support the sensing device 40. The bracket 56 comprises an arm 58 attached directly to the side of the tube 18 through a member 59. A plate 60 is attached to the arm 58 and sensing device 40 is mounted between the plate 60 and the wall of the tube 18.

Figure 4:
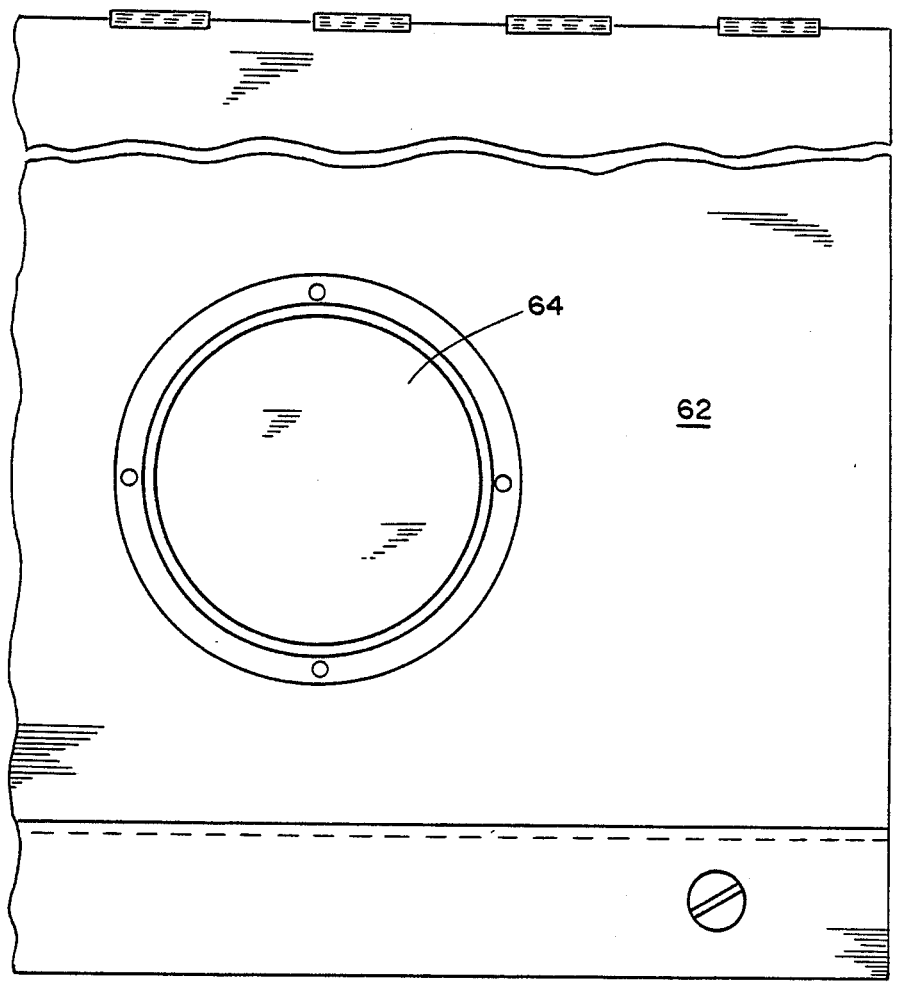
FIG. 4 is an elevational view showing a quartz window for use on a metering tube to allow for the installation of the near infrared detection apparatus.

The tube 18 is normally provided with an access door 62. This door may be modified as shown in FIG. 4 to include a circular window 64 which is made of quartz or any other material which is transparent in the near-infrared region. The instrument 40 is placed against the quartz window 64 such that the flowing column of tobacco is roughly perpendicular and at a fixed distance from the optical head of the instrument.

Figure 5:
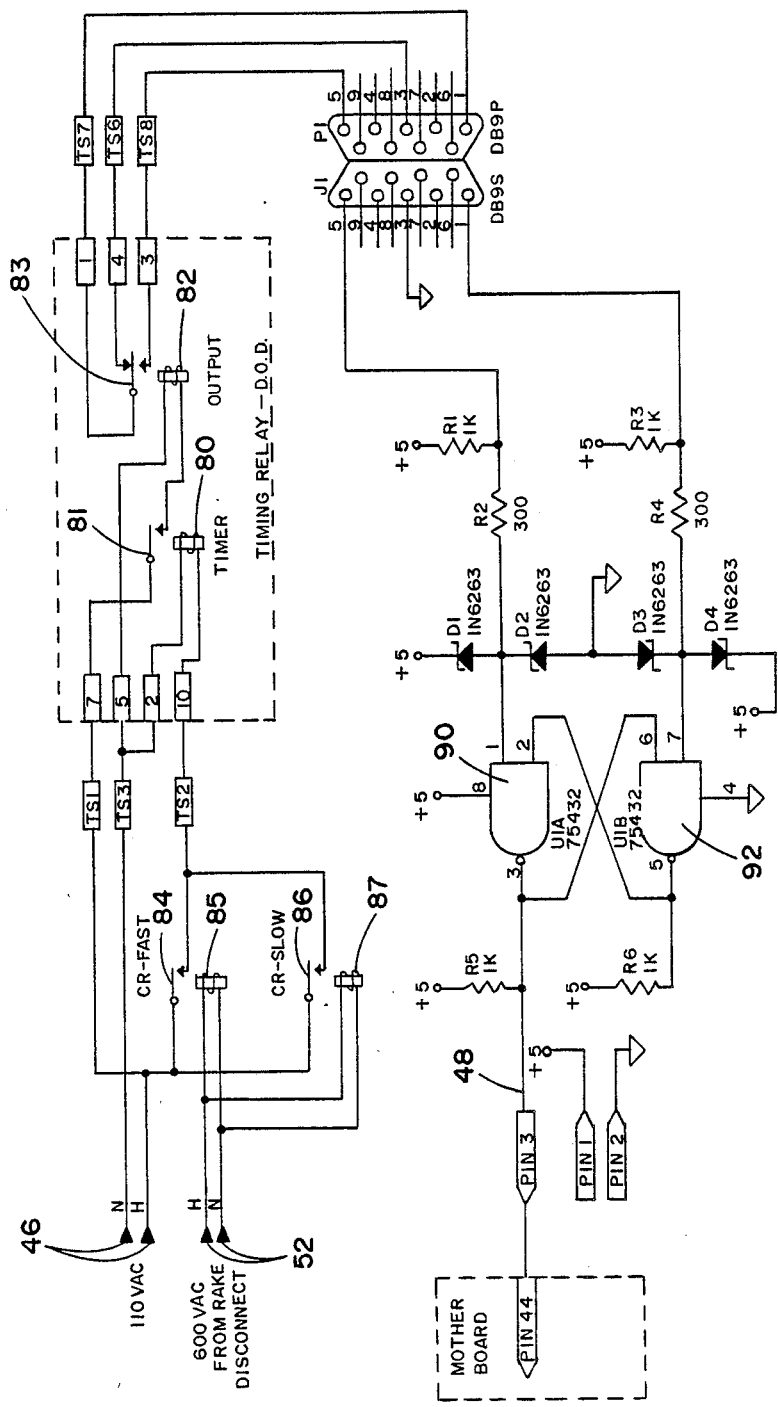
FIG. 5 is a schematic diagram showing the scan enable circuit of the present invention.

FIG. 5 shows the scan enable circuit 44 in greater detail. One set of input lines 46 is connected to the sensor 22, as discussed above. Another set of inputs is connected to the line 52 from the tachometer 50. It is noted that in the case of the conveyor being a pneumatic conveyor used with a rake in the metering tube 18, tachometer 50 can be connected to the rake shaft to indicate movement of tobacco. Alternatively, the signal can be derived from the motor driving current for the belt conveyor or the rake. In any case, when the tobacco is moving, a signal is present on line 46. This may be a 110 volt a.c. signal and is fed to one side each of two solenoid coils 80 and 82. The other side of each solenoid coil is connected to contacts 84 and 86, respectively, associated with two additional solenoid coils 85 and 87 which are connected across the inputs from line 52. Coil 85 is energized during high speed movement of the tobacco and coil 87 is energized during low speed movement of the tobacco. Thus, when the level of tobacco in metering tube 18 is within limits and the tobacco is moving either at high speed or at low speed, current is supplied to coil 80. Coil 80 pulls in contact 81 which energizes coil 82. Coil 82 switches contacts 83 to set a flip-flop formed from NAND gates 90 and 92. This sends a high signal through line 48 to the motherboard of the computer controlling the NIR spectrometer to enable the menthol sensing operation. The signal on line 48 is sensed by the computer through, for example, a standard interrupt routine. If the tobacco level moves out of the acceptable range the flip-flop is reset by coil 82 dropping out. If the tobacco stops moving, the flip-flop is reset after a time period determined by coil 80 which is a time delay operated coil. In this manner, as long as the level of tobacco is proper, the component sensing operation is conducted. This operation continues for a minimum length of time determined by the timing relay coil 80 and for a maximum length of time determined by the signal indicating movement of the tobacco.

Figure 6:
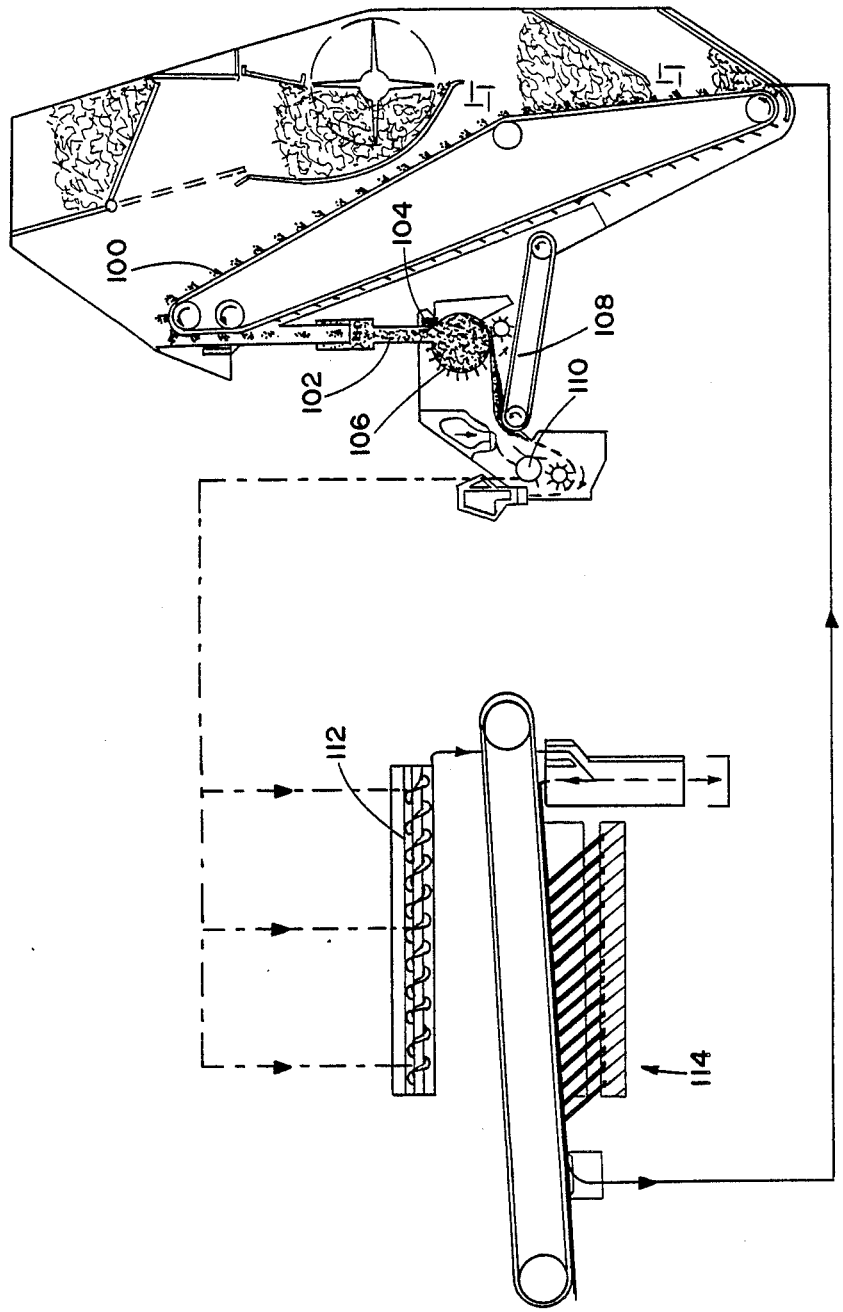
FIG. 6 is a part schematic drawing showing a cigarette maker.

The tobacco on conveyor 20 is fed to cigarette maker apparatus 26 in a conventional manner. The maker 26 is a conventional device which forms the tobacco into cigarettes. As shown in FIG. 6, the maker includes conventional components such as an automatic feed air lock and a conveyor system which includes a controlled steep angle conveyor 100 which deposits tobacco into a bulking chute 102 (sometimes also called the maker hopper) with a level sensor. The level of tobacco in the bulking chute 102 is maintained constant by the level sensor which controls the conveyor 100. The bulking chute 102 feeds the tobacco through a smoothing rail 104 into a needle roller 106 for fine metering of the tobacco. From here the tobacco is metered onto an apron 108 and then through a stem separator 110 into a spiral conveyor 112. The conveyor 112 feeds the tobacco into the rod forming machinery 114.

A full spectrum near infrared spectrometer can be mounted to the bulking chute 102 to analyze the tobacco as it about to be made into a cigarette rod. Normally one bulker 16 and metering tube 18 are used to feed a plurality of makers 26 so that a single NIR spectrometer can be used to analyze tobacco going to several makers. However, it has been observed that characteristics of tobacco such as moisture, menthol and the like can change as the tobacco is moved through the processing equipment. As a consequence it has been found that more reliable results can be obtained by using a separate NIR instrument for each maker. By mounting this equipment on the bulking chute 102, accuracy of the readings can be enhanced by virtue of the constant level maintained in the chute, as discussed above regarding metering tube 40.

It will be understood that the discussions above relating to modifications of the metering tube 18, including the NIR mount for the metering tube and the use of a scan enable circuit to ensure the readings are taken only when tobacco is moving and is at the proper height relate to the bulking chute as well.

The foregoing description is intended to illustrate the present invention without being limiting. Clearly numerous additions, substitutions and other changes can be made to the invention without departing from the scope thereof, as set forth in the appended claims. For example, as discussed briefly above, in the case of menthol sensing, the sensing apparatus can be placed between the menthol application apparatus and the bulker 16, rather than after the bulker. Before the bulker, the menthol evaporates from the tobacco until a state of equilibrium results after the mentholated tobacco sits in the bulker for a period of time. If the menthol concentration is determined immediately after menthol application, the results would have to be correlated with menthol values after the bulker in order for the data to be valid. Further, a NIR spectrometer may be mounted to any feed tube at any processing stage to monitor the condition of the tobacco at several locations.

What is claimed is:

1. An apparatus, comprising:
   means for moving a tobacco product;
   a feeding means having a vertical tube for feeding said tobacco product onto said moving means at a predetermined rate;
   means for maintaining a predetermined height of said tobacco product in said vertical tube; and
   a full spectrum near-infrared reflectance detection apparatus connected to said vertical tube to detect the concentration of at least one component in said tobacco product.

2. An apparatus as claimed in claim 1 wherein said full spectrum near-infrared detection apparatus comprises a broad spectrum light source.

3. An apparatus as claimed in claim 1 further including a cigarette making machine, said tobacco product being cigarette tobacco and said moving means being constructed and arranged to feed said cigarette tobacco to said making machine.

4. An apparatus as claimed in claim 3 further including a menthol application apparatus to add menthol to tobacco to produce said tobacco product and means for controlling operation of said menthol application apparatus in response to said infrared detection apparatus to maintain the concentration of menthol in a predetermined range.

5. An apparatus as claimed in claim 1 wherein said feeding means comprises a bulking chute of a cigarette maker.

6. An apparatus as claimed in claim 5 wherein said cigarette maker operates at least at a rate of approximately 7000 cigarettes per hour.

7. An apparatus as claimed in claim 1 wherein said moving means comprises a conveyor for feeding a plurality of cigarette making machines, each of said cigarette making machines having a separate feeder with a bulking chute.

8. An apparatus as claimed in claim 1 wherein said component comprises menthol.

9. An apparatus as claimed in claim wherein said component comprises sugar.

10. An apparatus as claimed in claim 1 wherein said component comprises moisture.

11. An apparatus as claimed in claim 1 wherein said component comprises nicotine.

12. An apparatus as claimed in claim 1 wherein said near infrared detection apparatus detects the concentration of a plurality of components in said tobacco product.

13. An apparatus, comprising:
a vertical metering tube for metering a product;
means for maintaining a predetermined height of product in said vertical metering tube;
means for receiving product from said vertical metering tube at a predetermined rate;
means for sensing a flow of product through said vertical metering tube;
means for determining the concentration of a predetermined component of said product while said product is flowing through said metering tube; and
means for interrupting the operation of said determining means if the flow of product through said metering tube stops.

14. An apparatus as claimed in claim 13 wherein said determining means comprises a near-infrared reflectance spectrometer.

15. An apparatus as claimed in claim 14 wherein said near infrared reflectance spectrometer comprises full spectrum near-infrared reflectance spectrometer.

16. An apparatus as claimed in claim 15 wherein said component is menthol and said product is tobacco.

17. An apparatus as claimed in claim 13 including means for controlling the concentration of said component in said product, wherein said controlling means is responsive to said determining means for maintaining the concentration of said component in a predetermined range.

18. A method, comprising:
feeding a product into a vertical metering tube;
metering said product from said vertical metering tube onto a product receiving line at a predetermined rate;
sensing a flow of product through said vertical metering tube;
determining the concentration of a predetermined component of said product while said product is flowing through said metering tube; and
halting the determining step if the flow of product through said metering tube stops.

19. A method as claimed in claim 18 including controlling the concentration of said component in said product responsive to said determining step for maintaining the concentration of said component in a predetermined range.

20. A method as claimed in claim 18 including sensing the height of product in said vertical metering tube and stopping the determining step if the height of said product in said metering tube should fall below a predetermined limit.

21. A method as claimed in claim 18 wherein said sensing step comprises sensing the presence of menthol using a near infrared reflectance spectrometer.

22. A method as claimed in claim 21 wherein said sensing step further comprises illuminating said product with full spectrum near-infrared radiation and detecting reflectance from said product.

* * * * *

UNITED STATES PATENT AND TRADEMARK OFFICE
CERTIFICATE OF CORRECTION

PATENT NO. : 4,971,077
DATED : November 20, 1990
INVENTOR(S) : Luis M. Dominguez et al.

It is certified that error appears in the above—identified patent and that said Letters Patent is hereby corrected as shown below:

Column 1, line 23, "form" should be --from--.

Column 4, line 28, "un" should be --run--.

Column 4, line 32, after "claim" insert --1--.

Signed and Sealed this

Twenty-sixth Day of May, 1992

Attest:

DOUGLAS B. COMER

Attesting Officer  Acting Commissioner of Patents and Trademarks